United States Patent
Wang et al.

(10) Patent No.: US 9,551,725 B2
(45) Date of Patent: Jan. 24, 2017

(54) CLEANLINESS MONITORING SYSTEM AND CARTRIDGES THEREOF

(75) Inventors: Yongqiang Wang, Guandong (CN); Chunhao Wu, Guandong (CN); Kunhsien Lin, Guandong (CN); Xiande Li, Guandong (CN); Minghu Qi, Guandong (CN); Weibing Yang, Guandong (CN); Zenghong Chen, Guandong (CN); Zhenhua Guo, Guandong (CN); Yunshao Jiang, Guandong (CN); Zhiyou Shu, Guandong (CN)

(73) Assignee: Shenzhen China Star Optoelectronics Technology Co., Ltd, Shenzhen, Guangdong (CN)

(*) Notice: Subject to any disclaimer, the term of this patent is extended or adjusted under 35 U.S.C. 154(b) by 714 days.

(21) Appl. No.: 13/641,098

(22) PCT Filed: Sep. 5, 2012

(86) PCT No.: PCT/CN2012/081000
§ 371 (c)(1),
(2), (4) Date: Oct. 13, 2012

(87) PCT Pub. No.: WO2014/032317
PCT Pub. Date: Mar. 6, 2014

(65) Prior Publication Data
US 2014/0067329 A1    Mar. 6, 2014

(30) Foreign Application Priority Data
Aug. 31, 2012 (CN) .......................... 2012 1 0316776

(51) Int. Cl.
G06F 15/00 (2006.01)
G01N 35/00 (2006.01)
G01N 15/00 (2006.01)

(52) U.S. Cl.
CPC . *G01N 35/00871* (2013.01); *G01N 2015/0046* (2013.01); *G01N 2035/00881* (2013.01)

(58) Field of Classification Search
CPC .................. G01N 35/00871; G01N 2015/0046; G01N 15/06; G01N 15/10; G06F 15/00
See application file for complete search history.

(56) References Cited

U.S. PATENT DOCUMENTS 6,009,381 A * 12/1999 Ono ............................... 702/188
6,009,383 A * 12/1999 Mony .................... G10L 19/005
                                                                455/418

(Continued)

FOREIGN PATENT DOCUMENTS

CN      202256115     *  5/2012
JP      200019095     *  1/2000

OTHER PUBLICATIONS

Zhang et. al.,"Dust particle online monitoring system for clean room", May 2012,CN202256115 (Bibligrapich;English).*

(Continued)

*Primary Examiner* — Hyun Park
*Assistant Examiner* — Mohammad Islam
(74) *Attorney, Agent, or Firm* — Andrew C. Cheng

(57) ABSTRACT

A system for monitoring cleanliness of a material handling system is disclosed. The system includes a measuring device, a first signal device, a second signal device, and a measuring host. The measuring device installed in the cartridges conduct the cleanliness measurements and obtains the measured result. The first signal device installed in the cartridges transforms the measured results to wireless signals. The second signal device installed in a predetermined location outside of the cartridges receives the wireless signal. The measuring host transforms the received wireless signals back to the measured results. The cartridges of the material handling system are also disclosed. The disclosed (Continued)

cleanliness monitoring system and the cartridge can reduce the cost.

3 Claims, 3 Drawing Sheets

(56) References Cited

U.S. PATENT DOCUMENTS

| | | | | |
|---|---|---|---|---|
| 7,439,855 | B1* | 10/2008 | Yufa | G01D 21/00 340/539.1 |
| 8,786,429 | B2* | 7/2014 | Li | G01S 5/02 205/687 |
| 2003/0016128 | A1* | 1/2003 | Lutz | G08C 19/00 340/517 |
| 2003/0216949 | A1* | 11/2003 | Kram | G06Q 10/02 705/5 |
| 2005/0253722 | A1* | 11/2005 | Droms | G08B 13/2402 340/572.1 |
| 2006/0046664 | A1* | 3/2006 | Paradiso | G08B 25/009 455/96 |
| 2007/0032245 | A1* | 2/2007 | Alapuranen | G08G 1/161 455/456.1 |
| 2007/0258421 | A1* | 11/2007 | Alizadeh-Shabdiz | G01S 5/0252 370/338 |
| 2009/0267776 | A1* | 10/2009 | Glenn | G08B 21/245 340/573.1 |
| 2011/0195701 | A1* | 8/2011 | Cook | G01S 5/0018 455/422.1 |
| 2012/0265370 | A1* | 10/2012 | Kim | G07C 5/0841 701/2 |
| 2014/0016483 | A1* | 1/2014 | Patel | H04L 43/50 370/252 |

OTHER PUBLICATIONS

Miyoko, "A cleanliness measurement device of a clean room, and a cleanliness measurement method of a clean room", Jan. 2000, JPO, JP200019095(English).*

Zhang et. al.,"Dust particle online monitoring system for clean room", May 2012,CN202256115 (Description;English).*

STIC, "Search report",May 28, 2015.*

Jang et. al. "Introduction to automated material handling system in LCD pannel production lines", IEEE, 1-4244-0311-1/06, Oct. 2006, 223-229.*

Zhang et. al.,"Dust particle online monitoring system for clean room", May 2012,CN202256115 (machine English translated).*

Miyoko, "A cleanliness measurement device of a clean room, and a cleanliness measurement method of a clean room", Jan. 2000, JPO, JP200019095(machine English translated).*

* cited by examiner

CLEANLINESS MONITORING SYSTEM AND CARTRIDGES THEREOF

BACKGROUND OF THE INVENTION

1. Field of the Invention

Embodiments of the present disclosure relate to environment monitoring technology, and more particularly to a cleanliness monitoring system and the cartridges thereof 2. Discussion of the Related Art Clean environments are needed for many technical fields, especially for factories manufacturing liquid crystal panels. The glasses for liquid crystal panels are transported by cartridges, and each of the cartridges may transport a few tens of glasses. The cartridges are transported by automatic material handling systems (AMHS) to corresponding stockers. The glasses are then retrieved from the cartridge by distributing devices in turns for corresponding manufacturing processes. After the manufacturing process, the glasses are transported back to the cartridges in turns, and the AMHS further transports the cartridge to another stocker for a next manufacturing process. The stocker and the tunnels connecting the stocker and the cartridges are part of the AMHS.

In manufacturing processes, the cleanliness of the environment directly affects the defective-free rate of the liquid crystal panels. As the defective rate results in significant costs for liquid crystal panels, each of the manufacturing processes of the liquid crystal panels has strict demands regarding the cleanliness. Especially, as the liquid crystal panels are deposited in the material handling system for the longest time, the cleanliness for the material handling system is the most critical one.

Currently, the cleanliness monitoring of the material handling system is conducted by a single measuring device operated by operators. The method has the following disadvantages. First, operators are also pollution sources. Second, the measuring device has to be shut down in some spots so that the capacity is reduced. Third, as the range of the factories is quite broad, a lot of measuring devices and the operators are needed so as to cover the range. For example, at least ten measuring devices are needed for the stocker with a length equaling to 60 meters, a width equaling to 6 meters, and a height equaling to 6 meters. Lastly, as the measurements are conducted by the operators, the hysteresis characteristic caused by the operators may result in the risk of defective rate.

SUMMARY in order to resolve the technical issues encountered by the prior art, the claimed invention introduce a technical solution by providing a cleanliness monitoring system and the cartridges thereof. Not only the monitoring efficiency may be enhanced, but also the cost may be reduced.

In one aspect, a system for monitoring cleanliness of a material handling system is disclosed. The material handling system includes a plurality of cartridges for loading materials. The material handling system transports the cartridges according to a predetermined route. The system includes a measuring device, a first signal device, a second signal device, a measuring host, and a printer. The measuring device conducts the cleanliness measurements and obtains the measured results. The measuring device is installed in the cartridges. The first signal device connects with the measuring device to receive the measured results and transforms the measured results to wireless signals. The first signal device is installed in the cartridges with at least one lithium battery supplying power to the measuring device and the first signal device. The second signal device receives the wireless signals, and is installed in a predetermined location outside of the cartridges. The measuring host connects with the second signal device to control the measuring device by the second signal device and the first signal device to conduct the cleanliness measurements so as to obtain the measured results and to receive the measured results. The measuring host transforms the received wireless signals back to the measured results. The printer connects to the measuring host, and is configured to print the measured results. The second signal device includes a plurality of wireless routers and a main router. The plurality of wireless routers connects with the first signal device by wireless communications to receive the wireless signals. The main router connects with the wireless routers to receive the wireless signals. The measuring host connects with the main router.

Wherein the plurality of wireless routers respectively connects to the main router and respectively corresponds to a plurality of measuring spots of the predetermined route. The measuring host controls the measuring device to conduct the cleanliness measurements by the first signal device and the second signal device, and to obtain location information and time information when the measuring device passes through each of the measuring spots.

Wherein the measuring host obtains the location information of the cartridges when the cartridges passes through each of the measuring spots, after obtaining the location information, the measuring host controls the measuring device to conduct the cleanliness measurements of each of the measuring spots by the first signal device and the second signal device and obtains the measured results of each of the measuring spots, and receives the time information and the wireless signals transformed from the measured results of each of the measuring spots.

Wherein the plurality of cartridges are installed with the measuring device and the first signal device.

In another aspect, a system for monitoring cleanliness of a material handling. system is disclosed. The material handling system includes a plurality of cartridges for loading materials, and the material handling system transports the cartridges according to a predetermined route. The system includes a measuring device, a first signal device, a second signal device, and a measuring host. The measuring device conducts the cleanliness measurements and obtains the measured results, and the measuring device is installed in the cartridges. The first signal device installed in the cartridges connects with the measuring device to receive the measured results and transforms the measured results to wireless signals. The second signal device receives the wireless signals, and the second signal device is installed in a predetermined location outside of the cartridges. The measuring host connects with the second signal device to receive the wireless signals and transforms the wireless signals hack to the measured results.

Wherein the measuring host controls the measuring device to conduct the cleanliness measurements by the second signal device and the first signal device so as to obtain the measured results.

Wherein the second signal device includes a plurality of wireless routers and a main router. The plurality of wireless routers connects with the first signal device by wireless communications to receive the wireless signals. The main router connects with the wireless routers to receive the wireless signals, and wherein the measuring host connects with the main router.

Wherein the plurality of wireless routers respectively connects to the main router and respectively corresponds to a plurality of measuring spots on the predetermined route, the measuring host controls the measuring device to conduct the cleanliness measurement by the first signal device and the second signal device, and to obtain a location information and a time information when the measuring device passes through each of the measuring spots.

Wherein the measuring host obtains the location information of the cartridges when the cartridges passes through each of the measuring spots, after obtaining the location information, the measuring host controls the measuring device to conduct the cleanliness measurements of each of the measuring spots by the first signal device and the second signal device and obtains the measured results of each of the measuring spots, and receives the time information and the wireless signals transformed from the measured results of each of the measuring spots.

Wherein the system further includes a printer connects to the measuring host, and is configured to print the measured results.

Wherein the cartridges includes at least one lithium battery to supply power to the measuring device and the first signal device.

Wherein the plurality of cartridges are installed with the measuring device and the first signal device.

In another aspect, a system for monitoring cleanliness of a material handling system is disclosed. The material handling system includes a plurality of cartridges or loading materials. The cartridges includes a measuring device conducting the cleanliness measurements and obtains the measured results, and a first signal device connecting with the measuring device to receive the measured results and transforms the measured results to wireless signals to be sent.

Wherein the measuring device obtains the measured results upon receiving the measuring instructions from a control host and transmits the measured result and the time information to the control host.

In view of the above, the cartridges and the measuring device within the cartridges routinely monitor the cleanliness of the material handling system. As only a few measuring devices are needed, the cost is thus reduced.

DETAILED DESCRIPTION OF THE EMBODIMENTS

Embodiments of the invention will now be described more fully hereinafter with reference to the accompanying drawings, in which embodiments of the invention are shown.

Figure 1:
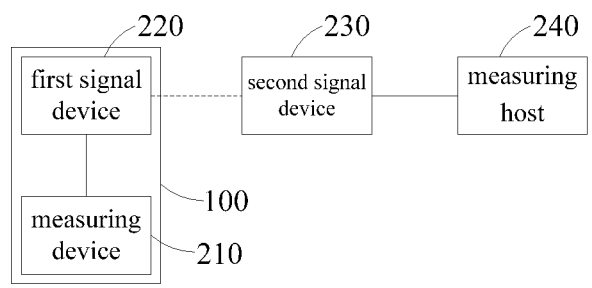
FIG. 1 is a schematic view of the structure of the cleanliness monitoring system in accordance with a preferred embodiment of the claimed invention.

FIG. 1 is a schematic view of the structure of the cleanliness monitoring system ("system") in accordance with a preferred embodiment of the claimed invention. The system is fir monitoring the cleanliness of a material handling system including a plurality of cartridges 100 loaded with materials. The material handling system routinely transports the cartridges 100 according to a predetermined route.

The system includes a measuring device 210, a first signal device 220, a second signal device 230, and a measuring host 240.

The measuring device 210 installed in the cartridge 100 conducts cleanliness measurements of the material handling system. As dust particles greatly affect the defective rate of the liquid crystal panels, the dust particles measurement is a critical measuring item. Thus, in the embodiment, the measuring device 210 may be a dust particle counter.

The first signal device 220 is installed in the cartridge 100. The first signal device 220 connects with the measuring device 210 to receive the measured results, and transforms the measured results to wireless signals that may be received and recognized by other devices. In the embodiment, the first signal device 220 may be a signal transmitter.

The second signal device 230 is installed in a predetermined location outside of the cartridge 100 to receive the wireless signals. As the wireless signals may be exchanged between the second signal device 230 and the first signal device 220, the location of the second signal device 230 may be arranged randomly. For example, the second signal device 230 is located in a specific spot on the predetermined route. When the cartridge 100 moves to the specific spot, the measuring device 210 conducts the cleanliness measurement accordingly, and then the first signal device 220 transmits the wireless signals to the second signal device 230.

The measuring host 240 connects with the second signal device 230 to receive the wireless signals and to transforms the wireless signals back to the measured results. In the embodiment, the measuring host 240 further controls the measuring device 210 to conduct the cleanliness measurements by the second signal device 230 and the first signal device 220.

The cartridge 100 may be loaded with the materials and routinely moves in the material handling system. Therefore, the measuring device 210 and the first signal device 220 may be installed in the cartridge 100 loaded with the materials or in an empty cartridge 100. When the cartridge 100 is routinely transported, the measuring device 210 is also routinely transported so as to conduct the cleanliness measurement within the range of the material handling system. In addition, the cartridge 100 with the measuring device 210 may be also mixed with the cartridge 100 only loaded with materials so that the cleanliness measurements may be conducted during the manufacturing processes without affecting the system capacity. Furthermore, by adopting the above routine cleanliness measurements, only a few measuring devices 210 have to be utilized and thus the efficiency may be enhanced and the cost may be reduced.

Figure 2:
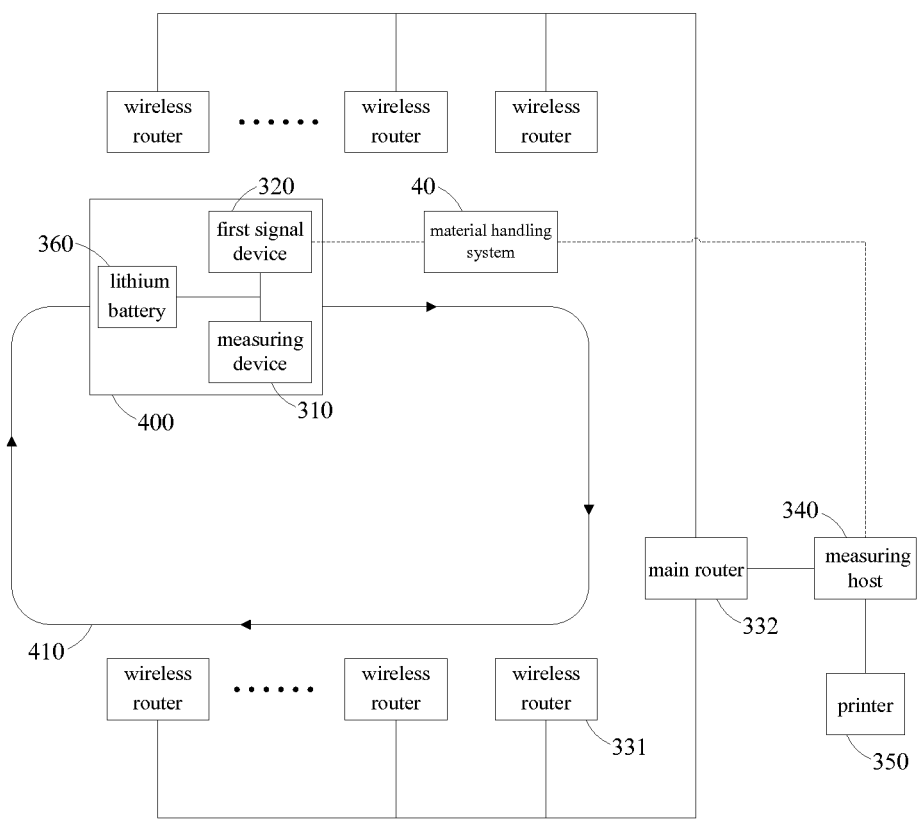
FIG. 2 is a schematic view of the structure of the cleanliness monitoring system in accordance with another embodiment of the claimed invention.

FIG. 2 is a schematic view of the structure of the cleanliness monitoring system in accordance with another embodiment of the claimed invention, in which the material handling system 40 is shown. The material handling system 40 includes a plurality of cartridges 400 for loading the materials. The material handling system 40 transports the cartridges 400 according to the predetermined route 410.

The cleanliness monitoring system monitoring the cleanliness of the material handling system 40 includes a measuring device 310, a first signal device 320, a second signal device 330, and a measuring host 340.

The measuring device 310 and the first signal device 320 are installed in the cartridges 400 and are connected with each other. The measuring device 310 conducts the cleanliness measurements for the material handling system 40 and obtains the measured results. The first signal device 320 receives the measured results and transforms the measured results to be the wireless signals.

The second signal device is installed in a predetermined location outside of the cartridge 400 to receive the wireless signals. The measuring host 340 connects with the second signal device to receive the wireless signals, and then transforms the wireless signals back to the measured results so as to control the measuring device 310 by the first signal device 320 and second signal device to conduct the cleanliness measurements.

In the embodiment, the second signal device 330 includes at least one wireless router 331 and a main router 332. The wireless router 331 connects with the first signal device 320 by the wireless communications to receive the wireless signals. The main router 332 connects with the wireless router 331 to receive the wireless signals. The measuring host 340 connects with the main router 332.

As the range of the material handling system 40 may be large, a plurality of measuring spots may be configured on the predetermined route 410 to ensure the measurement precision. Accordingly, a plurality of wireless routers 331 may be configured according to the plurality of measuring spots on the predetermined route 410. The plurality of wireless routers 331 respectively connects to the main router 332. The measuring host 340 controls the measuring device 310 to conduct the cleanliness measurements of each of the measuring spots by the first signal device 320 and the second signal device 330 when the measurement device 310 passes through each of the measuring spots. In addition, the measuring host 340 also obtains location information and time information when the measurement device 310 passes through each of the measuring spots.

As described above, the material handling system 40 connects with the measuring host 340 by cables or by the wireless communications. The measuring host 340 obtains the location information of the cartridges 400 when the cartridges 400 pass through the measuring spots. After obtaining the location information, the measuring host 340 controls the measuring device 310 to conduct the cleanliness measurement of each of the measuring spots by the first signal device 320 and the second signal device 330. The measuring host 340 obtains the measured results of each of the measuring spots, and receives the time information and the wireless signals.

The measuring host 340 further generates monitoring data from the location information, the time information, and the measured results transformed from the wireless signals of all of the measuring spots. The monitoring data may be presented by lists or by curve diagrams. With such monitoring data, the cleanliness and the change of the cleanliness of the material handling system 40 are demonstrated.

The material handling system 40 also includes a printer 350. The printer 350 connects to the measuring host 340 and is configured to print the measured results or the above mentioned lists or curve diagrams.

The cartridges 400 include at least one lithium battery 360 supplying the power to the measuring device 310 and the first signal device 320. In the embodiment, a plurality of cartridges 400 installed with the measuring device 310 and the first signal device 320 are arranged so as to increase the measurement frequency. In other embodiments, other types of batteries may be adopted to supply the power to the measuring device 310 and the first signal device 320.

The operating mechanism of the material handling system 40 of the embodiments is described below.

The predetermined route 410 is configured according to the range of the material handling system 40. The predetermined route 410 may be configured by the material handling system 40 or by the measuring host 340. Furthermore, the material handling system 40 may belong to manufacturing execution system (MES) in real scenarios, and thus the predetermined route 410 may be configured by the MES. After confirming the predetermined route 410, at plurality of measuring spots is configured on the predetermined route 410. The measuring host 340 obtains the location information of each of the measuring spots by the material handling system 40.

The material handling system 40 transports the cartridges 400 according to the predetermined route 410. The material handling system 40 notifies the measuring host 340 when the cartridges 400 arrives one of the measuring spots. After obtaining the location information, the measuring host 340 issues instructions by the second signal device 330 and the first signal device 320 to control the measuring device 310 to conduct the cleanliness measurements. In addition, the measurement host 340 obtains the time information from the material handling system 40. After the measuring device 310 obtains the measured results, the measuring host 340 receives the wireless signals by the second signal device 330 and the first signal device 320. The time information may be the time indicating when the measuring host 340 obtains the location information, the time indicating when the measuring device 310 conducts the cleanliness measurement, or the time indicating when the measuring host 340 receives the wireless signals. The above-mentioned time information corresponds to the location information of the measuring spots, and may be recorded and transmitted by the wireless router 331, the measuring device 310 with a timing function, or the material handling system 40.

The measuring host 340 may retrieve the location information from the wireless routers 331. The measuring host 340 assigns one IP address to each of the wireless router 331 corresponding to each of the measuring spots. In this way, each of the IP address corresponds to the location information of each of the measuring spots. When the cartridges 400 passes through the measuring spots, the wireless router 331 senses the first signal device 320 and establishes the wireless communication with the first signal device 320. The wireless router 331 transmits the location information corresponding to the IP address together with the wireless signals, and thus the measuring host 340 obtains the location information.

The cartridges 400 pass through other measuring spots and repeat the above process. When the cartridges 400 pass through the same measurement spot, though the location information remains unchanged, the time information has changed. Thus, the measured results may be recognized by the time information. The measuring host 340 analyzes the location information, the time information, and the measured results transformed from the wireless signals. The measurement host 340 then determines if the value of the cleanliness is above a threshold. The measuring host 340 further issues notifications when the value of the cleanliness is above the threshold so as to clean the pollution source in time.

When the range of the material handling system 40 is broad, multiple measuring spots may be configured in the cleanliness monitoring system. The system may be implemented by arranging only one measuring device 310 and by increasing the number of the wireless routers 331 at the same time. As the cost of the wireless routers 331 is lower than the measuring device 310, the cost of such implementation is lower.

Figure 3:
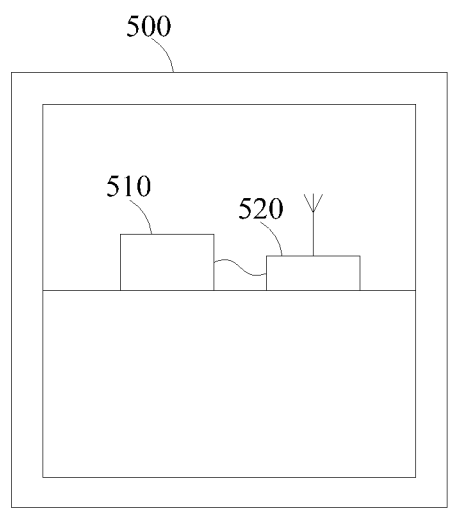
FIG. 3 is a schematic view of the structure of the cartridge transported by material handling system in accordance With a preferred embodiment of the claimed invention.

FIG. 3 is a schematic view of the structure of the cartridge transported by material handling system in accordance with a preferred embodiment of the claimed invention. In the embodiment, the cartridges 500 for loading the materials are part of the material handling system (not shown). The cartridges 500 include a measuring device 510 and a first signal device 520. The measuring device 510 conducts the cleanliness measurement to obtain the measured results. The first signal device 520 connects with the measuring device 510 to receive the measured results and then transforms the measured results to the wireless signals.

The measuring device 510 obtains the measured result upon receiving the measuring instructions and transmits the measured result and the time information to a control host. By adopting the above method, the cartridges and the measuring device within the cartridges routinely monitor the cleanliness within the range of the material handling system. As only a few measuring devices are needed, the cost is thus reduced.

It is believed that the present embodiments and their advantages will be understood from the foregoing description, and it will be apparent that various changes may be made thereto without departing from the spirit and scope of the invention or sacrificing all of its material advantages, the examples hereinbefore described merely being preferred or exemplary embodiments of the invention.

What is claimed is:

1. A system for monitoring cleanliness of a material handling system, the material handling system comprises a plurality of cartridges for loading materials, the material handling system transports the cartridges according to a predetermined route, the system comprising:
   a measuring device conducts the cleanliness measurements and obtains the measured results, the measuring device is installed in the cartridges;
   a first signal device connects with the measuring device to receive the measured results and transforms the measured results to wireless signals, the first signal device is installed in the cartridges with at least one lithium battery supplying power to the measuring device and the first signal device;
   a second signal device receives the wireless signals, the second signal device is installed in a predetermined location outside of the cartridges;
   a measuring host connects with the second signal device to control the measuring device by the second signal device and the first signal device to conduct the cleanliness measurement only when the cartridge moves to the predetermined location of the second signal device so as to obtain the measured results and to receive the measured results, and the measuring host transforms the received wireless signals back to the measured results;
   a printer connecting to the measuring host is configured to print the measured results;
   wherein the second signal device comprising:
   a plurality of wireless routers connecting with the first signal device by wireless communications to receive the wireless signals, the plurality of wireless routers respectively corresponds to a plurality of the measuring particular locations of the predetermined route, each of the wireless routers is assigned with one IP address corresponding to location information, and the wireless router transmits the location information and time information together with the wireless signals to the measuring host when the cartridge passes through a measuring particular location;
   a main router connecting with the wireless routers to receive the wireless signals;
   wherein the measuring host connects with the main router.

2. The system as claimed in claim 1, wherein the measuring host obtains the location information of the cartridges when the cartridges passes through each of the measuring particular locations, after obtaining the location information, the measuring host controls the measuring device to conduct the cleanliness measurements of each of the measuring particular locations by the first signal device and the second signal device and obtains the measured results of each of the measuring particular locations, and receives the time information and the wireless signals transformed from the measured results of each of the measuring particular locations.

3. The system as claimed in claim 1, wherein the plurality of cartridges are installed with the measuring device and the first signal device.

* * * * *